(12) United States Patent
Sugawara et al.

(10) Patent No.: US 9,234,966 B2
(45) Date of Patent: Jan. 12, 2016

(54) RADIATION IMAGING APPARATUS, METHOD OF CONTROLLING THE SAME, AND RADIATION IMAGING SYSTEM

(71) Applicant: CANON KABUSHIKI KAISHA, Tokyo (JP)

(72) Inventors: Eriko Sugawara, Honjo (JP); Toshio Kameshima, Kumagaya (JP); Tomoyuki Yagi, Honjo (JP); Katsuro Takenaka, Honjo (JP); Sho Sato, Saitama (JP); Atsushi Iwashita, Honjo (JP); Hideyuki Okada, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/803,234

(22) Filed: Mar. 14, 2013

(65) Prior Publication Data

US 2013/0264488 A1 Oct. 10, 2013

(30) Foreign Application Priority Data

Apr. 6, 2012 (JP) .................................. 2012-087936
Mar. 6, 2013 (JP) .................................. 2013-044726

(51) Int. Cl.
*G01T 1/00* (2006.01)
*G01T 1/16* (2006.01)
(Continued)

(52) U.S. Cl.
CPC .................. *G01T 1/16* (2013.01); *A61B 6/4233* (2013.01); *H01L 27/14658* (2013.01); *H04N 5/32* (2013.01); *H04N 5/376* (2013.01)

(58) Field of Classification Search
CPC .................................. G01T 1/171; G01T 1/247

USPC .......................................................... 250/394
See application file for complete search history.

(56) References Cited

U.S. PATENT DOCUMENTS 7,227,926 B2   6/2007  Kameshima et al. ......... 378/98.9
7,342,221 B2   3/2008  Takenaka et al. ........... 250/252.1
(Continued)

FOREIGN PATENT DOCUMENTS

CN   101448078   6/2009
CN   102313896   1/2012
(Continued)

OTHER PUBLICATIONS

Office Action issued on Sep. 28, 2014, in counterpart Chinese patent application 201310113288.9, with translation.
(Continued)

*Primary Examiner* — David Porta
*Assistant Examiner* — Edwin Gunberg
(74) *Attorney, Agent, or Firm* — Fitzpatrick, Cella, Harper & Scinto

(57) ABSTRACT

A radiation imaging apparatus including pixels; driving lines; a driving circuit; bias lines; an acquisition unit configured to acquire an evaluation value based on a current flowing in the bias line; a determination unit configured to compare the evaluation value with a comparison target value to determine whether radiation is irradiated; a control unit configured to control the acquisition unit and the determination unit; and a storage unit configured to store the evaluation value used in the determination process, is provided. A comparison target value used in a given determination process is based on one or more evaluation values used in one or more determination processes which are performed before the given determination process and in which it is determined that radiation has not been irradiated.

34 Claims, 9 Drawing Sheets

(51) Int. Cl.
  *H04N 5/32* (2006.01)
  *H04N 5/376* (2011.01)
  *A61B 6/00* (2006.01)
  *H01L 27/146* (2006.01)

(56) References Cited

U.S. PATENT DOCUMENTS

| | | |
|---|---|---|
| 7,386,089 B2 | 6/2008 | Endo et al. ............... 378/5 |
| 7,476,027 B2 | 1/2009 | Takenaka et al. .......... 378/207 |
| 7,491,960 B2 | 2/2009 | Takenaka et al. .......... 250/580 |
| 7,514,690 B2 | 4/2009 | Endo et al. ............... 250/370.14 |
| 7,573,038 B2 | 8/2009 | Yokoyama et al. ......... 250/370.09 |
| 7,696,484 B2 | 4/2010 | Yokoyama et al. ......... 250/370.09 |
| 7,839,977 B2 | 11/2010 | Kameshima et al. ........ 378/116 |
| 7,994,481 B2 | 8/2011 | Yagi et al. ............... 250/370.09 |
| 2008/0309802 A1* | 12/2008 | Widenhorn et al. ........ 348/243 |
| 2009/0272909 A1 | 11/2009 | Takenaka et al. .......... 250/270.09 |
| 2010/0086102 A1 | 4/2010 | Kameshima et al. ........ 378/62 |
| 2011/0309262 A1 | 12/2011 | Sato et al. ............... 250/393 |
| 2011/0317054 A1 | 12/2011 | Kameshima et al. ........ 348/302 |
| 2011/0317809 A1 | 12/2011 | Eguchi ................... 378/62 |
| 2012/0001079 A1 | 1/2012 | Okada .................... 250/366 |
| 2012/0097860 A1* | 4/2012 | Oguma ................... 250/394 |
| 2012/0132820 A1* | 5/2012 | Iwakiri et al. ........... 250/370.08 |

FOREIGN PATENT DOCUMENTS

| | | |
|---|---|---|
| EP | 0 603 709 A2 | 6/1994 |
| JP | 2010-268171 | 11/2010 |
| JP | 2011-185622 | 9/2011 |
| WO | WO 00/65825 A | 11/2000 |

OTHER PUBLICATIONS

EESR issued on Jul. 23, 2015, in counterpart EPA 13161565.0 (in Eng).

* cited by examiner

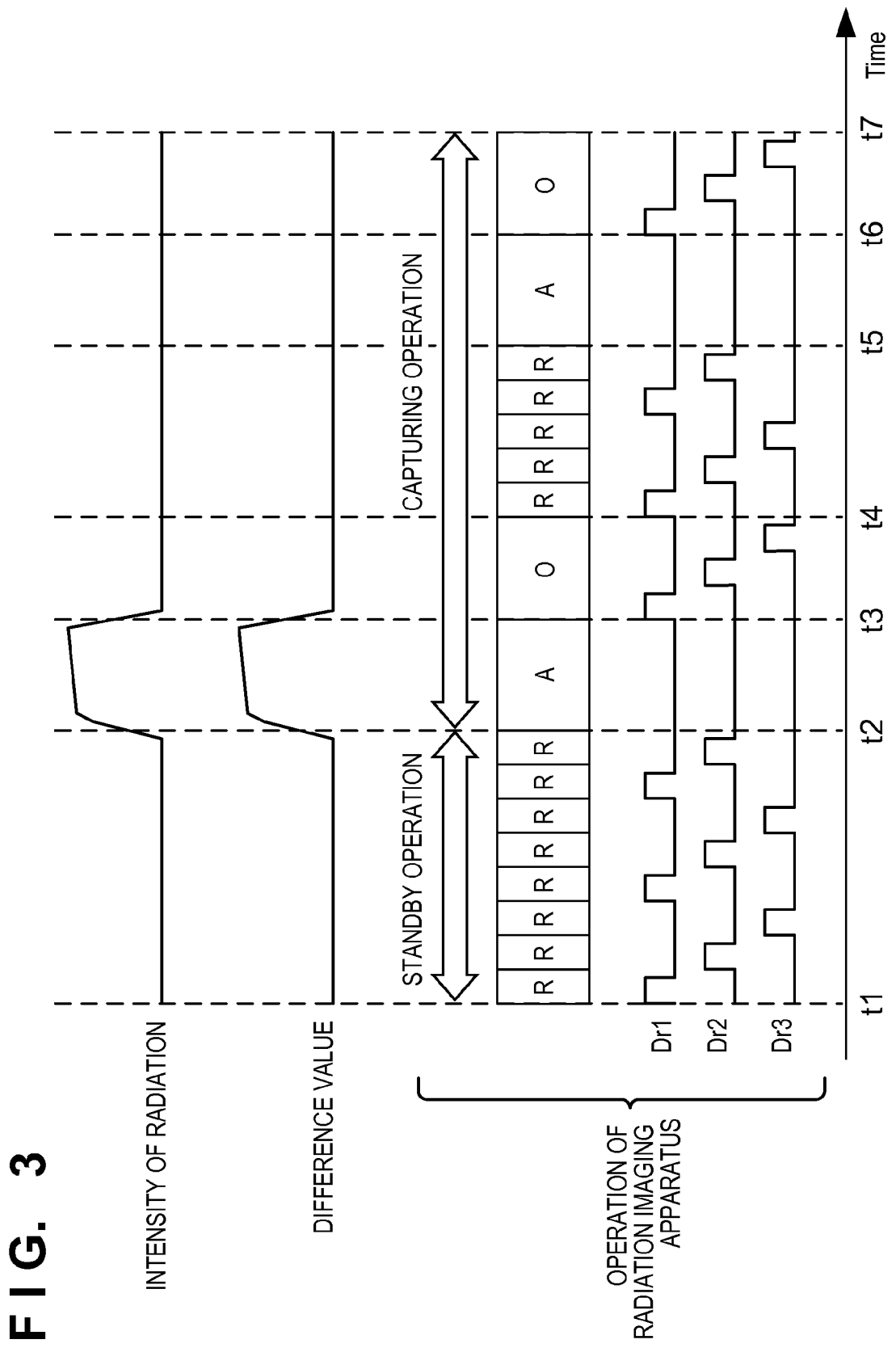

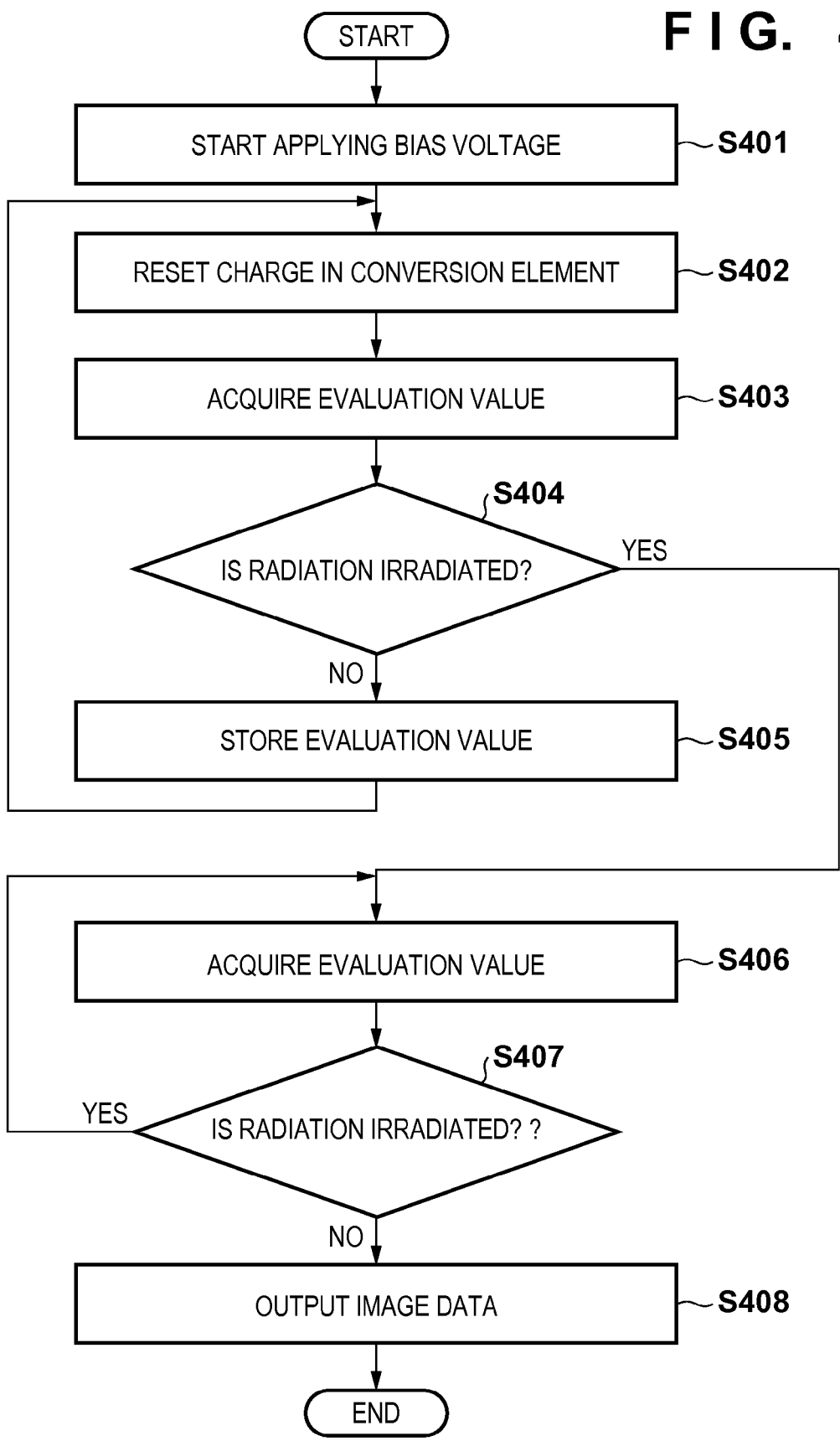

FIG. 5A

| I[K-3, 1] | I[K-2, 1] | I[K-1, 1] | I[K, 1] |
|---|---|---|---|
| I[K-3, 2] | I[K-2, 2] | I[K-1, 2] | EVALUATION VALUE AS DETERMINATION TARGET |
| I[K-3, 3] | I[K-2, 3] | I[K-1, 3] | |

FIG. 5B

| I[K-3, 1] | I[K-2, 1] | I[K-1, 1] | I[K, 1] |
|---|---|---|---|
| I[K-3, 2] | I[K-2, 2] | I[K-1, 2] | EVALUATION VALUE AS DETERMINATION TARGET |
| I[K-3, 3] | I[K-2, 3] | I[K-1, 3] | |

FIG. 5C

| I[K-3, 1] | I[K-2, 1] | I[K-1, 1] | I[K, 1] |
|---|---|---|---|
| I[K-3, 2] | I[K-2, 2] | I[K-1, 2] | EVALUATION VALUE AS DETERMINATION TARGET |
| I[K-3, 3] | I[K-2, 3] | I[K-1, 3] | |

FIG. 5D

| I[K-3, 1] | I[K-2, 1] | I[K-1, 1] | I[K, 1] |
|---|---|---|---|
| I[K-3, 2] | I[K-2, 2] | I[K-1, 2] | EVALUATION VALUE AS DETERMINATION TARGET |
| I[K-3, 3] | I[K-2, 3] | I[K-1, 3] | |

F I G.  9A

| Io[K-1, 1] | Ie[K-1, 2] | Io[K, 1] |
|---|---|---|
| Io[K-1, 3] | Ie[K-1, 4] | EVALUATION VALUE AS DETERMINATION TARGET |
| Io[K-1, 5] | Ie[K-1, 6] | |

F I G.  9B

| Io[K-1, 1] | Ie[K-1, 2] | Io[K, 1] |
|---|---|---|
| Io[K-1, 3] | Ie[K-1, 4] | EVALUATION VALUE AS DETERMINATION TARGET |
| Io[K-1, 5] | Ie[K-1, 6] | |

F I G. 10
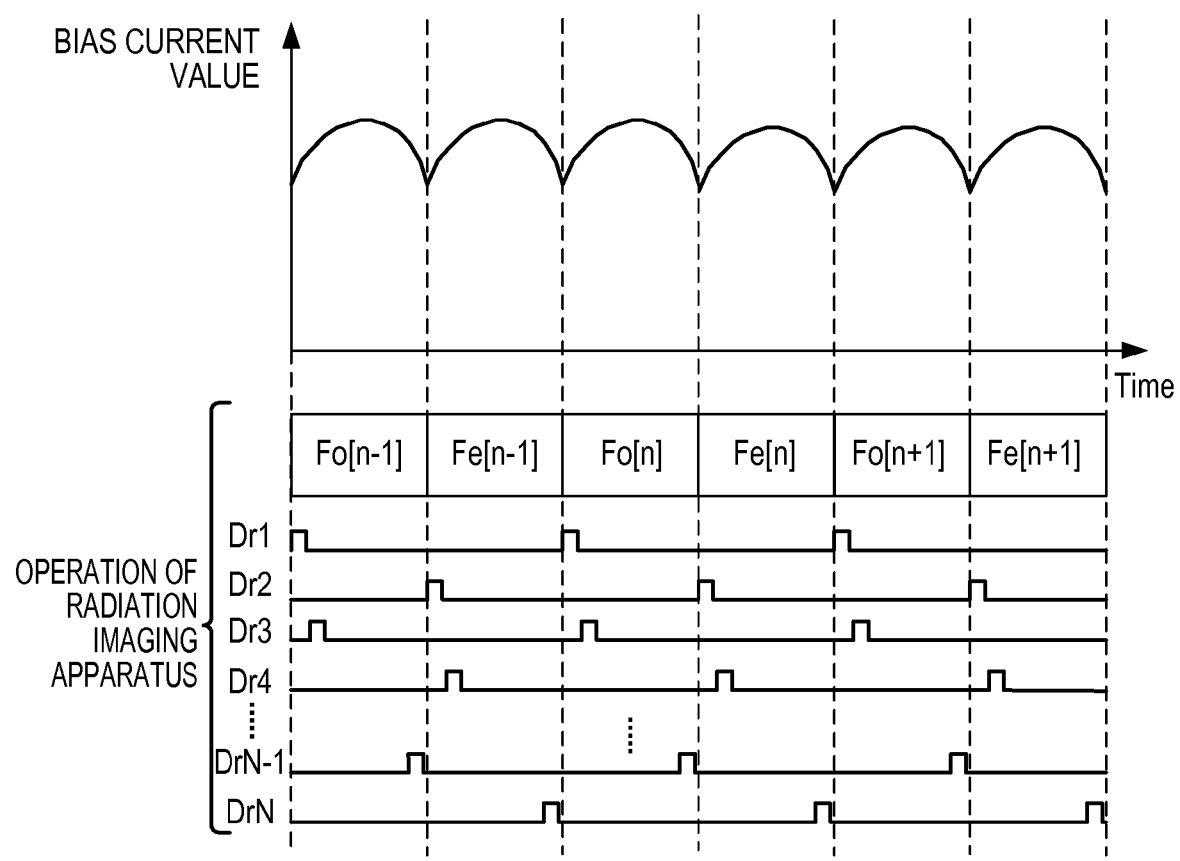

RADIATION IMAGING APPARATUS, METHOD OF CONTROLLING THE SAME, AND RADIATION IMAGING SYSTEM

BACKGROUND OF THE INVENTION

1. Field of the Invention

The present invention relates to a radiation imaging apparatus, a method of controlling the same, and a radiation imaging system.

2. Description of the Related Art

Recently, medical imaging diagnosis and nondestructive inspection with radiation such as X-rays have been performed by using a radiation imaging apparatus which can output digital images. Japanese Patent Laid-Open No. 2010-268171 proposes a radiation imaging apparatus which automatically determines whether radiation is irradiated from a radiation generating apparatus. This radiation imaging apparatus includes a plurality of pixels. Each pixel includes a conversion element which converts X-rays or light into charge and a switching element which can apply a desired voltage to one of the electrodes of the conversion element. A bias voltage is applied to the other electrode of the conversion element via a bias line. When radiation is irradiated onto the pixel, a current flows in the bias line. By using this, each pixel determines whether radiation is irradiated. The above radiation imaging apparatus resets the voltages applied to the conversion elements by sequentially setting the switching elements of the pixels in a conductive state for each row, thereby transferring the electrical signal based on the dark charge accumulated in each conversion element via the switching element. This sequentially resets the conversion elements. This reset operation causes the current which does not originate from radiation to flow in the bias line. In order to avoid a determination error due to this current, this apparatus performs the above determination upon subtraction of the waveform of this current stored in advance, when actually using a radiation generating apparatus. When the apparatus sequentially and repeatedly resets conversion elements as disclosed in Japanese Patent Laid-Open No. 2010-268171, the current generated by this reset operation changes depending on which row of conversion elements is reset. For this reason, the radiation imaging apparatus disclosed in Japanese Patent Laid-Open No. 2011-185622 is designed to measure, in advance, a profile of currents generated at the time of resetting for all the columns of conversion elements at factory shipment or the like and perform a subtraction process by using the profile.

SUMMARY OF THE INVENTION

The radiation imaging apparatus disclosed in the above literature performs a subtraction process by using the current value obtained in advance by tests at factory shipment or the like. However, the current flowing in each bias line depends on the state of the radiation imaging apparatus when it measures the current. For example, the current value based on the dark charge flowing in the bias line can vary in a test at factory shipment and at the time of actual use. For this reason, it is not possible to determine the irradiation of radiation with sufficient accuracy even when correcting the current flowing in the bias line by using the current value obtained in advance by tests. An aspect of the present invention provides a technique of improving the accuracy of determination on whether radiation is irradiated onto a radiation imaging apparatus.

An aspect of the present invention provides a radiation imaging apparatus comprising: a plurality of pixels each including a conversion element configured to convert radiation into charge and a switching element configured to transfer an electrical signal based on the charge; a plurality of driving lines respectively connected to the switching elements which differ from each other; a driving circuit configured to apply conductive voltage to the plurality of driving lines to set the switching elements in a conductive state; bias lines for applying bias voltage to the conversion elements of the plurality of pixels to make the conversion elements convert radiation into charge; an acquisition unit configured to perform an acquisition process of an evaluation value based on a current flowing in the bias line; a determination unit configured to perform a determination process of comparing the evaluation value with a comparison target value to determine whether radiation is irradiated onto the conversion element; a control unit configured to control the acquisition unit and the determination unit to perform the acquisition process and the determination process a plurality of times; and a storage unit configured to store the evaluation value used in the determination process, wherein a comparison target value used in a given determination process is based on one or more evaluation values used in one or more determination processes which are performed before the given determination process and in which it is determined that radiation has not been irradiated.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention, and together with the description, serve to explain the principles of the invention.

FIG. 3 is a chart for explaining an example of the operation of the radiation imaging apparatus according to some embodiments;

FIG. 4 is a flowchart for explaining an example of the operation of the radiation imaging apparatus according to some embodiments;

FIGS. 5A to 5D are views for explaining an example of the stored contents of an evaluation value memory according to some embodiments;

FIGS. 9A and 9B are views for explaining an example of the stored contents of an evaluation value memory 207 according to an embodiment of the present invention; and FIG. 10 is a chart for explaining an example of the transition of a dark current according to an embodiment of the present invention.

DESCRIPTION OF THE EMBODIMENTS

Figure 1:
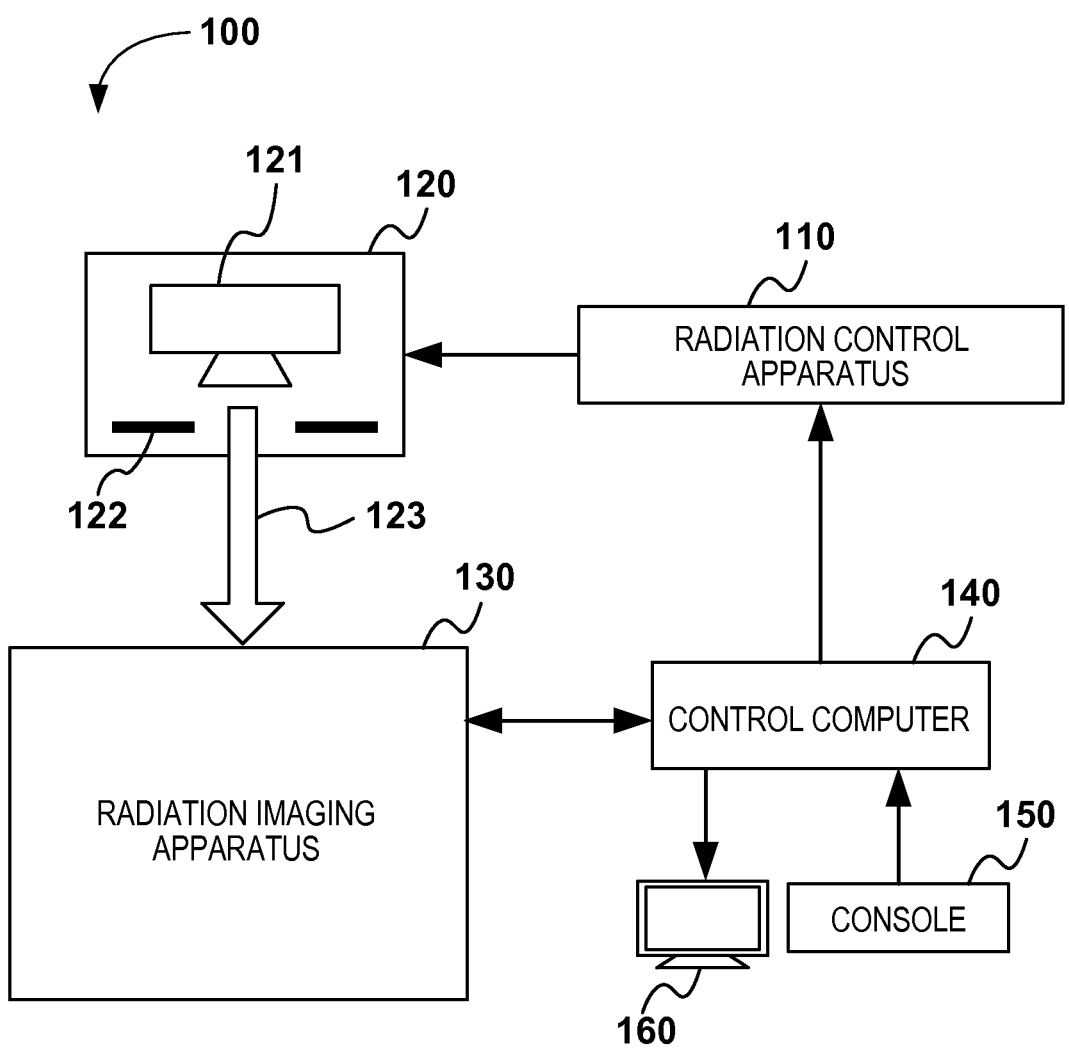
FIG. 1 is a block diagram for explaining the arrangement of a radiation imaging system according to some embodiments.

The embodiments will be described below with reference to the accompanying drawings. The same reference numerals denote the same elements throughout various embodiments, and a repetitive description of them will be omitted. In addition, the respective elements can be changed and combined as needed.

An example of the arrangement of a radiation imaging system 100 according to various embodiments will be described first with reference to FIG. 1. The radiation imaging system 100 is used for still image capturing such as general imaging and moving image capturing such as fluoroscopy in, for example, medical diagnosis. The radiation imaging system 100 can include a radiation control apparatus 110, a radiation generating apparatus 120, a radiation imaging apparatus 130, a control computer 140, a console 150, and a display device 160.

The radiation control apparatus 110 controls the operations of a radiation source 121 and an exposure field aperture mechanism 122 which are included in the radiation generating apparatus 120. The radiation source 121 exposes radiation 123 toward the radiation imaging apparatus 130 in response to an instruction from the radiation control apparatus 110. In this case, the radiation 123 can include beams such as α-rays, β-rays, and γ-rays which generate particles (including photons) emitted by radiation destruction, and beams having similar energies, such as X-rays, particle rays, and cosmic rays. The exposure field aperture mechanism 122 can adjust an exposure field as a region irradiated with the radiation 123 in the radiation imaging apparatus 130. The radiation 123 exposed by the radiation source 121 is transmitted through an object (not shown) and reaches the radiation imaging apparatus 130.

The radiation imaging apparatus 130 generates image data corresponding to the radiation 123 irradiated toward the apparatus itself, and transmits the data to the control computer 140. This transmission may be performed by wireless communication or wired communication. A detachable memory in the radiation imaging apparatus 130 may store the generated image data. The user of the radiation imaging system 100 may manually move this memory to the control computer 140. The radiation imaging apparatus 130 according to this embodiment can determine whether the radiation 123 is irradiated onto the apparatus itself. Upon determining that the radiation 123 is irradiated onto the apparatus, it can automatically start generating image data.

The control computer 140 processes the image data received from the radiation imaging apparatus 130 and displays the resultant image on the display device 160. The control computer 140 controls the operations of the radiation control apparatus 110 and radiation imaging apparatus 130 in accordance with the input operation performed by the user via the console 150. For example, the control computer 140 may transmit radiation exposure conditions to the radiation control apparatus 110 or may transmit parameters and the like which define operation to the radiation imaging apparatus 130.

Figure 2:
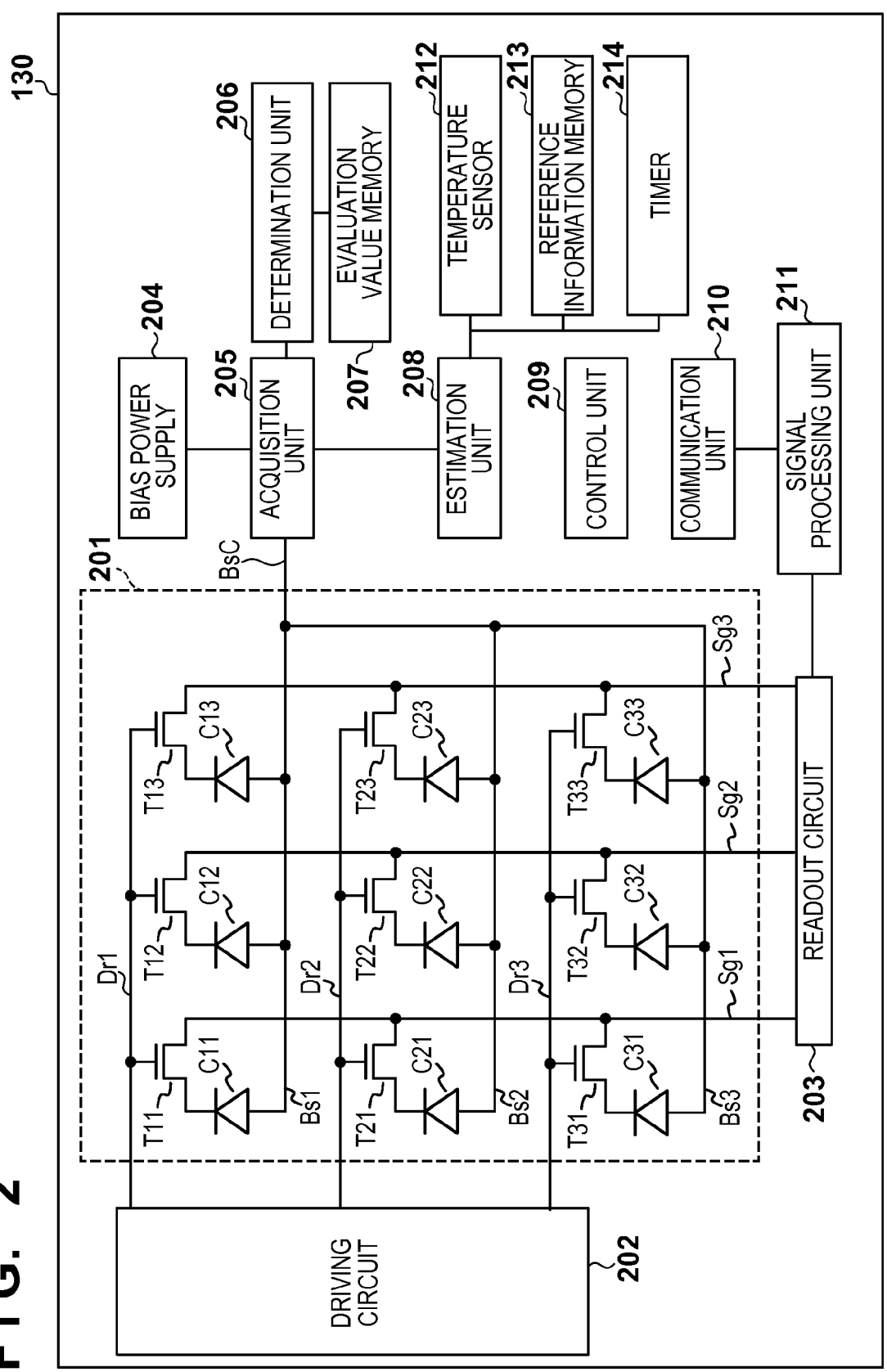
FIG. 2 is a view for explaining an example of the arrangement of the radiation imaging apparatus according to some embodiments.

An example of the detailed arrangement of the radiation imaging apparatus 130 described above will be described next with reference to FIG. 2. Although the radiation imaging apparatus 130 can include various components shown in FIG. 2, the apparatus may not include some of the components depending on the embodiments. The components used in each embodiment will be described in detail below.

A detection unit 201 includes a plurality of pixels arranged in an array form. Each pixel includes a conversion element and a transistor. Referring to FIG. 2, the pixels are arranged in three rows and three columns. However, this embodiment can be applied to an arbitrary number of pixels. Each conversion element and each transistor which are included in i row×j column ($1 \leq i \leq 3$, $1 \leq j \leq 3$) pixels will be respectively referred to as a conversion element $C_{ij}$ and a transistor $T_{ij}$. These elements will be collectively termed a conversion element C and a transistor T. One driving line Dri and one bias line Bsi are arranged for ith-row ($1 \leq i \leq 3$) pixels. Driving lines Dr1 to Dr3 and bias lines Bs1 to Bs3 will be collectively termed a driving line Dr and a bias line Bs. One signal line Sgj is placed for jth-column ($1 \leq j \leq 3$) pixels. Signal lines Sg1 to Sg3 will be collectively termed a signal line Sg.

The conversion element C converts the radiation 123 irradiated onto the radiation imaging apparatus 130 into charge. The conversion element C may directly convert the radiation 123 into charge or may convert the light converted from the radiation 123 by the scintillator (not shown) of the radiation imaging apparatus 130 into charge. As the conversion element C, for example, a PIN photodiode may be used, which is disposed on an insulating substrate such as a glass substrate and is made of amorphous silicon as a chief material. The first electrode (e.g., cathode) of the conversion element C is connected to the first main electrode of the transistor T. The second electrode (e.g., anode) of the conversion element C is connected to the bias line Bs.

The transistor T functions as a switching element for connecting the conversion element C and the signal line Sg, and is, for example, a thin-film transistor (TFT). Another type of switching element may be used instead of the transistor T. The first main electrode (e.g., source) of the transistor T is connected to the first electrode of the conversion element C. The second main electrode (e.g., drain) of the transistor T is connected to the signal line Sg. The control electrode (e.g., gate) of the transistor T is connected to the driving line Dr. When the transistor T is ON (in a conductive state), the electrical signal based on the charge accumulated in the conversion element C is transferred to the signal line Sg. At this time, the power supply connected to the signal line Sg applies a desired voltage to the first electrode of the conversion element C to reset the charge in the conversion element C, thereby resetting the conversion element C. The power supply connected to the signal line Sg is, for example, the reference power supply of the amplification circuit provided for a readout circuit 203 (to be described later) for each signal line Sg. When the transistor T is OFF (in a non-conductive state), the charge accumulated in the conversion element C is not reset. Note that this switching element is not limited to the one connected to the signal line Sg and may be, for example, a switching element which is different from the switching element connected to the signal line Sg and is connected to the power supply without the intervention of the signal line Sg to transfer an electrical signal from the conversion element C to the power supply.

A driving circuit 202 outputs a driving signal having a conductive voltage and a non-conductive voltage to the driving line Dr to switch the transistor T between a conductive state and a non-conductive state. When, for example, setting the transistor T in a conductive state, the driving circuit 202 applies a conductive voltage to the driving line Dr. When setting the transistor T in a non-conductive state, the driving circuit 202 applies a non-conductive voltage to the driving line Dr. When the driving circuit 202 applies a conductive voltage to the driving line Dr, the electrical signal based on the charge accumulated in the conversion element is transferred to the signal line Sg via the transistor T connected to the driving line Dr, thereby removing the accumulated charge. That is, the driving circuit 202 functions as a reset unit which resets the charge accumulated in the conversion element.

The readout circuit 203 reads out an electrical signal from the signal line Sg and outputs the signal as digital image data to a signal processing unit 211. The readout circuit 203 can include, for example, an amplification circuit for amplifying a read electrical signal, a sample/hold circuit for sampling and holding the amplified signal, and an A/D converter for converting the held analog signal into a digital signal.

A bias power supply 204 applies a bias voltage to be applied to the bias line Bs. When the bias voltage is applied to the conversion element C, the semiconductor layer of the conversion element C is depleted. This allows the conversion element to convert radiation or light into charge. The bias lines Bs1 to Bs3 merge to one bias line BsC. The bias power supply 204 can apply bias voltage to the bias lines Bs1 to Bs3 by applying a bias voltage to the bias line BsC via an acquisition unit 205.

The acquisition unit 205 acquires an evaluation value based on the current value (to be referred to as the bias current value hereinafter) of a current (to be referred to as a bias current hereinafter) flowing in the bias line BsC. The acquisition unit 205 may use a bias current value as an evaluation value without any change or may use a voltage value obtained by a bias current as an evaluation value. Alternatively, the acquisition unit 205 may acquire, as an evaluation value, a current value after a bias current is filtered by using a low-pass filter or bandpass filter. An evaluation value may be an instantaneous current value of a bias current or an integral value in a given period. In some embodiments, the acquisition unit 205 converts an evaluation value into a digital value by using an A/D converter and outputs the evaluation value after the conversion to a determination unit 206. The sampling frequency of the A/D converter can be two or more times the frequency of the operation of acquiring an evaluation value by the acquisition unit 205.

The determination unit 206 compares the evaluation value acquired by the acquisition unit 205 with a comparison target value to determine whether the radiation 123 is irradiated onto the radiation imaging apparatus 130. The operation of the determination unit 206 will be described in detail later. An estimation unit 208 estimates the value of the dark current included in the bias current measured by the acquisition unit 205. The operation of the estimation unit 208 will be described in detail later. A temperature sensor 212 measures a temperature in the radiation imaging apparatus 130. A reference information memory 213 stores reference information which is referred to by the estimation unit 208 to estimate the value of a dark current. A timer 214 has a timepiece function. An evaluation value memory 207 functions as a storage unit which stores the evaluation value acquired by the acquisition unit 205.

The signal processing unit 211 processes the image data output from the readout circuit 203. A communication unit 210 communicates with the control computer 140 and transmits, for example, the image data generated by the signal processing unit 211 to the control computer 140 or transmits the instruction received from the control computer 140 to a control unit 209. The control unit 209 controls the overall operation of the radiation imaging apparatus 130. More specifically, the control unit 209 performs the operation described with reference to the following flowchart. For the sake of simplicity, the illustration of lines connecting the control unit 209 to the respective components is omitted in FIG. 2.

FIG. 3 is a chart for explaining an example of a series of operations from the power-on of the radiation imaging apparatus 130 to the output of still image data. The upper graph portion in FIG. 3 represents the intensity of the radiation 123 irradiated onto the radiation imaging apparatus 130. The intermediate graph portion in FIG. 3 represents the difference value between the evaluation value calculated by the determination unit 206 and the comparison target value. The lower graph portion in FIG. 3 represents the operation of the radiation imaging apparatus 130 and indicates the timings of the driving signals supplied to the driving lines Dr.

The power supply of the radiation imaging apparatus 130 is turned on at time t1 to start applying a bias voltage to the bias line Bs. This makes the radiation imaging apparatus 130 start standby operation. The control unit 209 then controls the driving circuit 202 to repeat the reset operation indicated by "R" in FIG. 3. The driving circuit 202 performs this reset operation by sequentially applying conductive voltages to the plurality of driving lines Dr and sequentially setting the transistors T in a conductive state for each row. The control unit 209 controls the acquisition unit 205 and the determination unit 206 so as to make the acquisition unit 205 acquire the evaluation value based on a bias current while the driving circuit 202 is performing this reset operation and make the determination unit 206 determine whether radiation is irradiated onto the conversion element C.

If a difference value falls outside a threshold range at time t2, the determination unit 206 determines that the irradiation of the radiation 123 has started. The control unit 209 terminates the standby operation by stopping the application of a conductive voltage from the driving circuit 202, and starts capturing operation. First of all, the control unit 209 starts the accumulating operation represented by "A" in FIG. 3. In the accumulating operation A, the control unit 209 stops the application of a conductive voltage from the driving circuit 202, and hence sets all the transistors T in a non-conductive state. This will accumulate, in the pixel, the electrical signal based on the charge converted from radiation by the conversion element C.

When the difference value falls inside the threshold range at time t3, the determination unit 206 determines that the irradiation of the radiation 123 has stopped, and the control unit 209 terminates the accumulating operation A. The control unit 209 then starts readout operation ("O" in FIG. 3) in which the transistor T transfers the accumulated electrical signal to the signal line Sg. The control unit 209 performs the readout operation O, like reset operation, by making the driving circuit 202 sequentially apply driving voltages to the plurality of driving lines Dr so as to sequentially set the transistors T in a conductive state for each row. When the readout operation O stops, the control unit 209 controls the driving circuit 202 at time t4 to repeat the reset operation indicated by "R" several times. The control unit 209 may perform this reset operation without controlling the acquisition unit 205 and the determination unit 206. The reset operation is preparatory operation for the acquisition of image data based on a dark current which starts at time t5, and hence is not required to detect the irradiation of radiation. When the control unit 209 terminates reset operation in preparatory operation after the application of a conductive voltage to a driving line Drk (k is one of 1 to 3) by the driving circuit 202, the control unit 209 may also terminate reset operation in capturing operation by applying a conductive voltage to the same driving line Drk. In the case shown in FIG. 3, since the standby operation ends after the application of a conductive voltage to the driving line Dr2, the control unit 209 terminates reset operation in capturing operation after the application of a conductive voltage to the same driving line Dr2.

The control unit 209 performs the accumulating operation indicted by "A" in FIG. 3 at time t5. In the accumulating operation A, since the radiation 123 is not irradiated, the charge accumulated in the conversion element C is dark charge. This dark charge accumulating operation may be performed in only the same period as that of the accumulating operation for the charge based on the radiation 123 (that is, the control unit 209 performs accumulating operation to hold t3−t2=t6−t5). At time t6, the control unit 209 starts reading out the electrical signal based on the dark charge indicated by "O" and generates image data in accordance with the read electrical signal. This data corresponds to the image data based on the dark charge. At time t7, the control unit 209 obtains the difference between the two obtained image data by using the signal processing unit 211, and transmits the obtained image data from the communication unit 210 to the control computer 140. The operation from time t3 to time t7 corresponds to capturing operation.

An example of the operation of the radiation imaging apparatus 130 will be described next with reference to FIG. 4. The operation indicated by the flowchart of FIG. 4 starts when, for example, the power supply of the radiation imaging apparatus 130 is turned on or when the control computer 140 issues a request to start operation. The user of the radiation imaging system 100 can expose the radiation 123 from the radiation generating apparatus 120 and capture an image at an arbitrary time after the start of this operation. The radiation imaging apparatus 130 can automatically detect the irradiation of the radiation 123, generate image data, and transmit the data to the control computer 140.

In step S401, the bias power supply 204 starts applying a bias voltage to the bias line Bs. The bias voltage is applied to the bias line BsC via the acquisition unit 205. The control unit 209 subsequently repeats the processing from step S402 to step S405 until determining in step S404 that radiation is irradiated. In step S402, the control unit 209 controls the driving circuit 202 to reset the charge accumulated in an arbitrary conversion element C by applying a conductive voltage to an arbitrary driving line Dr. Dark charge is accumulated in the conversion element C regardless of whether the radiation 123 is irradiated. The conversion element C is reset to remove this dark charge. In some embodiments, the driving circuit 202 applies a conductive voltage to any one of the driving lines Dr (one of the driving lines Dr1 to Dr3) in one reset operation (one execution in step S402). In other embodiments, the driving circuit 202 may simultaneously apply conductive voltages to a plurality of driving lines Dr in one reset operation. For example, the driving circuit 202 may simultaneously apply conductive voltages to the two driving lines Dr in one reset operation or to all the driving lines Dr in the detection unit 201. That is, the control unit 209 may reset conversion elements on a group basis.

In step S403, the control unit 209 controls the acquisition unit 205 to acquire an evaluation value based on a bias current value. The acquisition unit 205 may acquire an evaluation value by using an instantaneous bias current value flowing in the bias line BsC or an integral value of bias current values flowing during the interval between the previous acquisition and the current acquisition.

In step S404, the determination unit 206 determines whether the radiation 123 is irradiated onto the conversion element C, in response to the acquisition of an evaluation value by the acquisition unit 205. That is, in step S404, the determination unit 206 determines whether the irradiation of the radiation 123 onto the conversion element C has started. The determination unit 206 may determine whether the difference between the evaluation value acquired in step S403 and a comparison target value falls inside a threshold range. The comparison target value depends on one or more evaluation values stored in the evaluation value memory 207. The way in which the determination unit 206 acquires a comparison target value will be described later. The determination unit 206 outputs the determination result to the control unit 209. If the difference between the two values falls inside the threshold range, the determination unit 206 determines that the radiation 123 is not irradiated (NO in step S404), and the control unit 209 advances to step S405. If the difference between the two values does not fall inside the threshold range, the determination unit 206 determines that the radiation 123 is irradiated (YES in step S404), and the control unit 209 advances to step S406. In step S405, the determination unit 206 stores the evaluation value acquired in step S403 in the evaluation value memory 207. Thereafter, the control unit 209 returns to step S402 to repeat the processing from step S402 to step S405. That is, the driving circuit 202 continues the sequential application of conductive voltages to a plurality of driving lines Dr.

Upon determining in step S404 that the irradiation of the radiation 123 has started, the control unit 209 stops the application of a conductive voltage to the driving line Dr by the driving circuit 202, and starts accumulating operation. The control unit 209 repeats the processing in steps S406 and S407 until determining in step S407 that the radiation 123 is not irradiated. In this repetition, since the charge in the conversion element C is not reset, the electrical signal based on the charge originating from the radiation 123 is accumulated in the pixel. The processing in steps S406 and S407 is the same as that in steps S403 and S404. In step S407, the determination unit 206 determines whether the irradiation of the radiation 123 onto the radiation imaging apparatus 130 is complete. The threshold range used in the determination process in step S404 may be equal to or different from that used in the determination process in step S407. Upon determining in step S407 that the radiation 123 is not irradiated (NO in step S407), the control unit 209 advances to step S408. Upon determining in step S407 that the radiation 123 is irradiated (YES in step S407), the control unit 209 returns to step S406 to repeat the processing in steps S406 and S407.

Upon determining in step S407 that the irradiation of the radiation 123 is complete, the control unit 209 controls the driving circuit 202 to make the transistor T transfer the electrical signal accumulated in the pixel in the detection unit 201 to the signal line Sg in step S408. The readout circuit 203 reads out the electrical signal from the pixel and outputs it as image data to the control computer 140.

The determination processes performed by the determination unit 206 in FIG. 4 will be described in detail next. In the following description, the driving circuit 202 applies conductive voltages to the driving lines Dr one by one in the reset process in step S402. That is, the driving circuit 202 resets conversion elements C11 to C13 by applying a conductive voltage to the driving line Dr1 in a given reset process. The driving circuit 202 resets conversion elements C21 to C23 by applying a conductive voltage to the driving line Dr2 in the next reset process. The driving circuit 202 resets conversion elements C31 to C33 by applying a conductive voltage to the driving line Dr3 in the next reset process. Upon completing the application of the conductive voltage to the driving line Dr3, the driving circuit 202 resets the conversion elements C11 to C13 by applying a conductive voltage to the driving line Dr1 again in the next reset process. The unit of the period during which all the conversion elements C in the detection unit 201 each are reset once will be referred to as a frame.

The evaluation value acquired by the acquisition unit 205 varies due to the influences of dark currents and the like even when the radiation 123 is not irradiated onto the radiation imaging apparatus 130. When, therefore, the determination unit 206 uses a fixed value obtained in advance by tests at factory shipment or the like as a comparison target value, it is necessary to set a wide threshold range to avoid determination errors due to the influences of dark currents and the like. In this case, it takes much time for the difference value between an evaluation value and the comparison target value to exceed the threshold range, resulting in the inability to accurately detect the start of the irradiation of radiation. For example, in spite of the fact that the irradiation of radiation has started, the apparatus may determine that no radiation has been irradiated. The same applies to the case of the detection of the end of irradiation of radiation. That is, in spite of the fact that the irradiation of radiation has stopped, the apparatus may determine that radiation has been irradiated. In various embodiments, the comparison target value used in steps S404 and S407 described above is based on the evaluation value used in a determination process before the execution of these steps and is not the fixed value obtained in advance by tests at factory shipment or the like.

FIGS. 5A to 5D are views each for explaining an example of the value stored in the evaluation value memory 207 which is referred to by the determination unit 206 to acquire a comparison target value. FIGS. 5A to 5D are views each for explaining an evaluation value to be referred to in the determination processes in steps S404 and S407. The evaluation value memory 207 stores these evaluation values to be referred to. Referring to FIGS. 5A to 5D, I[i, j] represents the evaluation value acquired by the acquisition unit 205 in step S403 after the application of a conductive voltage to a driving line Drj (j=1, 2, 3) in step S402 in the ith frame (i≥1). For example, I[K, 1] represents the evaluation value acquired by the acquisition unit 205 after the application of a conductive voltage to the driving line Dr1 in the Kth frame.

In some embodiments, the determination unit 206 performs a determination process in step S404 by using the evaluation value used in the previous determination process as a comparison target value. This evaluation value is the one used in the last one of one or more previous determination processes in which the determination unit 206 has determined that the radiation 123 has not been irradiated. Consider a case in which the determination unit 206 performs a determination process in step S404 by using an evaluation value I[K, 2] ("determination target evaluation value" in FIG. 5A) acquired in step S403 after the application of a conductive voltage to the driving line Dr2 in step S402 in the Kth frame. As indicated by the thick line frame in FIG. 5A, the evaluation value memory 207 stores, at this point of time, an evaluation value I[K, 1] stored by the determination unit 206 upon previous execution of step S405. The determination unit 206 determines in step S404 whether the difference value between the evaluation values I[K, 2] and I[K, 1] as a comparison target value, that is, I[K, 2]–I[K, 1], falls inside the threshold range. It is thought that the dark current flowing in the bias line BsC changes little in two consecutive acquiring operations. Using the evaluation value used in the previous determination process as a comparison target value can therefore reduce the width of the threshold range and improve the accuracy of determination on whether the irradiation of the radiation 123 has started.

Upon determining that the difference value falls inside the threshold range, the determination unit 206 stores the evaluation value I[K, 2] in the evaluation value memory 207 in step S405. In this case, the determination unit 206 may overwrite the stored evaluation value I[K, 1]. This can save a memory capacity. Upon determining that the difference value does not fall inside the threshold range, the determination unit 206 may not store the evaluation value I[K, 2] in the evaluation value memory 207. When determining in step S407 whether the irradiation of the radiation 123 has stopped, the determination unit 206 needs to use, as a comparison target value, an evaluation value in a state in which the radiation 123 is not irradiated. That is, upon determining in step S407 that the difference between the acquired evaluation value and the evaluation value in a state in which the radiation 123 is not irradiated falls inside the threshold range, the determination unit 206 can determine that the acquired bias current includes no current originating from the radiation 123. The evaluation values acquired after the evaluation value I[K, 2] are influenced by the radiation 123, and hence the determination unit 206 does not use these evaluation values as comparison target values in the determination process in step S407. In step S407, the determination unit 206 uses, as a comparison target value, the evaluation value I[K, 1] used in the last one of one or more previous determination processes in which the determination unit 206 has determined that the radiation 123 has not been irradiated.

In other embodiments, the determination unit 206 performs a determination process in step S404 by using, as a comparison target value, the value calculated from a plurality of evaluation values acquired in a plurality of previous determination processes. This evaluation value is calculated from a plurality of evaluation values used in a plurality of last determination processes of one or more previous determination processes in which the determination unit 206 has determined that the radiation 123 has not been irradiated. Consider a case in which the determination unit 206 performs a determination process by using the evaluation value I[K, 2] acquired after the application of a conductive voltage to the driving line Dr2 in step S402 in the Kth frame. As indicated by the thick line frame in FIG. 5B, the evaluation value memory 207 stores, at this point of time, three evaluation values I[K−1, 2] to I[K, 1] stored by the determination unit 206 upon three previous executions of step S405. The determination unit 206 determines in step S404 whether the difference value between the evaluation value I[K, 2] and an average value AVG of I[K−1, 2] to I[K, 1] as a comparison target value, that is, I[K, 2]–AVG, falls inside a threshold range. In the above case, three evaluation values corresponding to one frame are used to calculate a comparison target value. However, the number of evaluation values to be used is not specifically limited. In addition, it is possible to weight the respective evaluation values when obtaining an average value. For example, it is possible to obtain an average value upon assigning higher weights to the evaluation values acquired at later times. Alternatively, it is possible to assign higher weights to evaluation values acquired after the application of conductive voltages to the same driving line Dr. Calculating a comparison target value from a plurality of evaluation values used in a plurality of consecutive determination processes can reduce variations in acquired evaluation value and reduce the width of a threshold range. This makes it possible to improve the accuracy of determination on whether the irradiation of the radiation 123 has started.

Upon determining that the difference value falls inside the threshold range, the determination unit 206 stores the evaluation value I[K, 2] in the evaluation value memory 207 in step S405. In this case, the determination unit 206 may overwrite the oldest evaluation value I[K−1, 1] among stored evaluation values. This can save a memory capacity. Upon determining that the difference value does not fall inside the threshold range, the determination unit 206 may not store the evaluation value I[K, 2] in the evaluation value memory 207 for the same reason as that in the above embodiments. In step S407, the determination unit 206 uses, as a comparison target value, the value calculated from the plurality of evaluation values I[K−1, 2] to I[K, 1] used in a plurality of last determination processes of one or more previous determination processes in which the determination unit 206 has determined that the radiation 123 has not been irradiated.

In other embodiments, the determination unit 206 performs a determination process in step S404 by using the evaluation value previously acquired after the application of a conductive voltage to the same driving line Dr. Consider a case in which the determination unit 206 performs a determination process by using the evaluation value I[K, 2] acquired after the application of a conductive voltage to the driving line Dr2 in step S402 in the Kth frame. As shown in FIG. 5C, the evaluation value memory 207 stores, at this point of time, the three evaluation values I[K−1, 2] to I[K, 1] stored by the determination unit 206 in the previous three executions of step S405. The determination unit 206 uses, as a comparison target value, the evaluation value I[K−1, 2] used in the last one of one or more previous determination processes in which a conductive voltage has been applied to the same driving line Dr2 as that in the current determination process and the determination unit 206 has determined that the radiation 123 has not been irradiated. The evaluation value I[K−1, 2] is surrounded by the thick line frame in FIG. 5C. The determination unit 206 determines in step S404 whether the difference value between the evaluation values I[K, 2] and I[K−1, 2] as a comparison target value, that is, I[K, 2]−I[K−1, 2], falls inside the threshold range.

Figure 6:
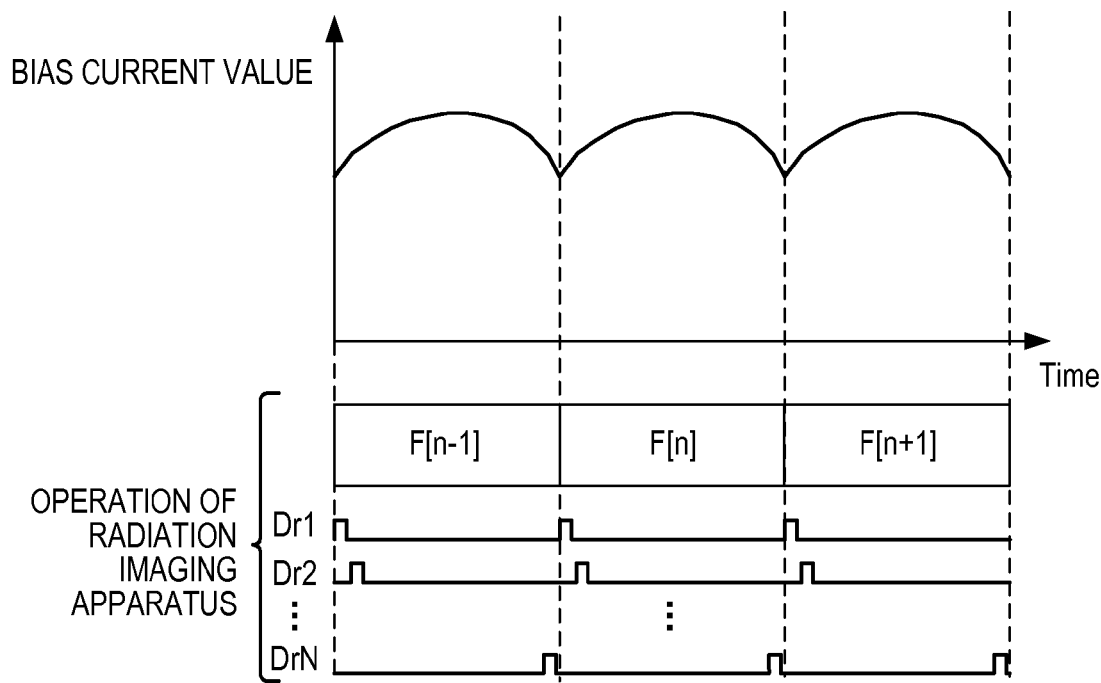
FIG. 6 is a chart for explaining an example of the transition of a bias current according to some embodiments.

The effect obtained by performing a determination process by using the evaluation value I[K−1, 2] previously acquired upon application of a conductive voltage to the same driving line Dr2 will be described with reference to FIG. 6. FIG. 6 is a graph of an evaluation value after the lapse of a sufficient period of time since the power supply of the radiation imaging apparatus 130 is turned on. F[n] represents a period during which the radiation imaging apparatus 130 executes the nth frame. In each frame, conductive voltages are sequentially applied to the driving lines Dr to reset the conversion elements C. Switching the transistor T between a conductive state and a non-conductive state by applying a conductive voltage to the transistor will cause a current to flow in a bias line Br connected to the same pixel as that to which the driving line Dr is connected. This current is included in the bias current measured by the acquisition unit 205. The present inventors found that a bias current value varies depending on to which driving line Dr a conductive voltage is applied even in the same frame. This seems to be caused by variations in the parasitic capacitance of the transistor T connected to the driving line Dr or the capacitance of the conversion element C. If the variations are large, using the evaluation value used in a previous determination process as a comparison target value is equivalent to comparing evaluation values originating from the application of conductive voltages to the different driving lines Dr. This makes it difficult to accurately detect the irradiation of radiation.

The present inventors, however, found that the waveforms of bias currents are similar on a frame basis. For example, as shown in FIG. 6, the waveform of a bias current in a frame F[n−1], the waveform of a bias current in a frame F[n], and the waveform of a bias current in a frame F[n+1] are similar to each other. That is, the evaluation values obtained upon application of conductive voltages to the same driving line Dr become similar to each other even in different frames. It is therefore possible to improve the accuracy of determination by making the determination unit 206 perform a determination process by using, as a comparison target value, the evaluation value I[K−1, 2] previously acquired upon application of a conductive voltage to the same driving line Dr.

Upon determining that the difference value falls inside the threshold range, the determination unit 206 stores the evaluation value I[K, 2] in the evaluation value memory 207 in step S405. In this case, the determination unit 206 may overwrite the oldest evaluation value I[K−1, 1] among the stored evaluation values. This can save a memory capacity. Upon determining that the difference value does not fall inside the threshold range, the determination unit 206 may not store the evaluation value I[K, 2] in the evaluation value memory 207 for the same reason as that described in the above embodiments. In step S407, the determination unit 206 uses, as a comparison target value, the evaluation value I[K−1, 2] used in the last one of one or more determination processes which have been previously performed for the same driving line Dr and in which the determination unit 206 has determined that the radiation 123 has not been irradiated.

In other embodiments, the determination unit 206 performs a determination process by using, as a comparison target value, the value calculated from a plurality of evaluation values previously acquired after the application of conductive voltages to the same driving line Dr. Consider a case in which the determination unit 206 performs a determination process by using the evaluation value I[K, 2] acquired after the application of a conductive voltage to the driving line Dr2 in step S402 in the Kth frame. At this point of time, the evaluation value memory 207 stores six evaluation values I[K−2, 2] to I[K, 1] stored in the determination unit 206 upon six previous executions of step S405. The determination unit 206 uses, as a comparison target value, the value calculated from evaluation values used in a plurality of last determination processes of previous determination processes in which conductive voltages have been applied to the same driving line Dr2 and the determination unit 206 has determined that the radiation 123 has not been irradiated. These evaluation values are I[K−3, 2], I[K−2, 2], and I[K−1, 2] indicated by the thick line frames in FIG. 5D. The determination unit 206 determines in step S404 whether the difference value between the evaluation value I[K, 2] and an average value AVG of the evaluation values in the thick line frames, that is, I[K, 2]−AVG, falls within the threshold range. The determination unit 206 determines in step S404 whether the difference value between the evaluation value I[K, 2] and the average value AVG as a comparison target value falls inside the threshold range. In the above case, three evaluation values corresponding to three frames are used for the calculation of a comparison target value. However, the number of evaluation values to be used is not specifically limited. As in the above embodiments, the determination unit 206 performs weighting as needed to calculate a comparison target value. Processing in step S405 and a determination process in step S407 are the same as those in the above embodiments.

Each embodiment described above uses the same method to acquire a comparison target value used in the determination process in step S404 and a comparison target value used in the determination process in step S407. However, each embodiment may use different methods. For example, it is possible to perform the determination process in step S404 by using the evaluation value I[K, 1] used in the previous determination process and to perform the determination process in step S407 by using the value AVG calculated from evaluation values used in a plurality of previous determination processes.

Figure 7:
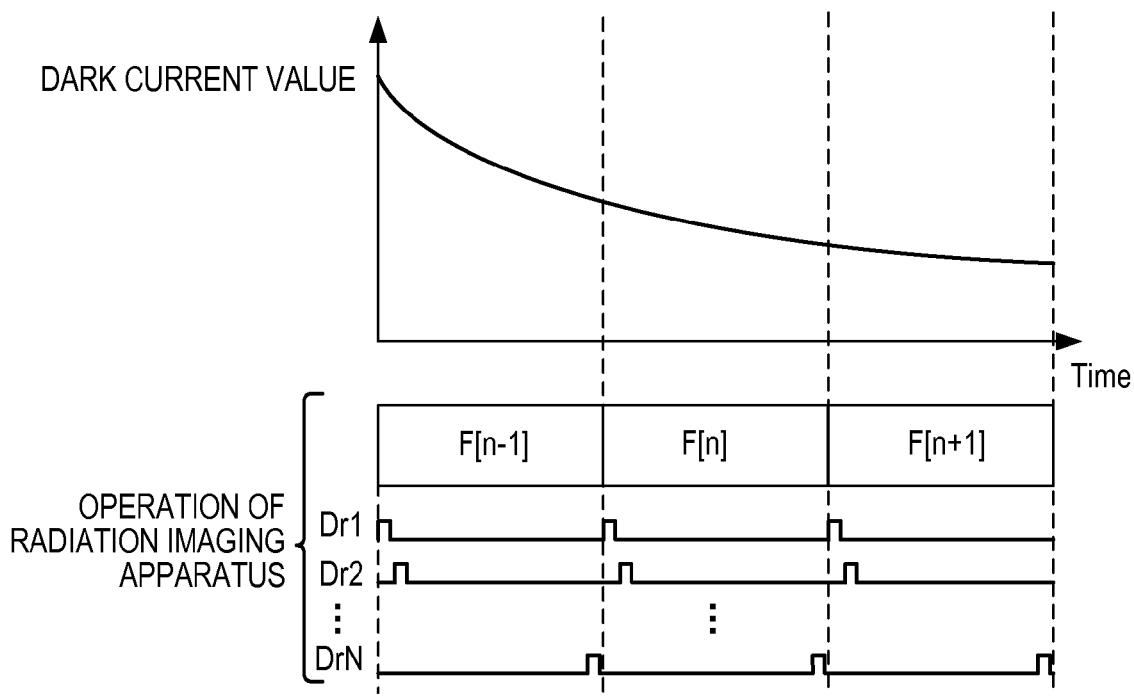
FIG. 7 is a chart for explaining an example of the transition of a dark current according to some embodiments.

According to the description with reference to FIG. 6, in the state in which a sufficient period of time has elapsed since the power supply of the radiation imaging apparatus 130 was turned on, the dark currents generated in the detection unit 201 in the respective frames become almost the same value. However, the dark current generated immediately after the power supply of the radiation imaging apparatus 130 is turned on increases for each frame. For example, the dark current immediately after the power supply of the radiation imaging apparatus 130 is turned on changes as shown in FIG. 7. In a frame F[1] executed immediately after the power supply of the radiation imaging apparatus 130 is turned on, the dark current value is large. This value gradually decreases to converge to a predetermined value with the lapse of time. A cause of a dark current is that when the voltage applied to a conversion element varies, a current flows in the conversion element, and the movement of charge due to the current influences a defect level. A dark current tends to take a large value when the temperature of the conversion element is high, immediately after the conversion element C is optically reset by using a light source such as an LED or EL, or immediately after the start of irradiation of radiation.

In some embodiments, the determination unit 206 performs determination processes in steps S404 and S407 in FIG. 4 in consideration of an estimated value of a dark current. It is possible to combine these embodiments with an arbitrary one of the above embodiments. In steps S403 and S406 in FIG. 4, the acquisition unit 205 outputs, as an evaluation value, the value obtained by subtracting an estimated value of the dark current estimated to be included in a bias current flowing in the bias line BsC from the bias current to the determination unit 206. The estimation unit 208 calculates an estimated value of a dark current. The estimation unit 208 acquires a bias current value as a function of the state of the radiation imaging apparatus 130, and stores the value in the reference information memory 213 before the start of the operation based on the flowchart of FIG. 4, for example, at factory shipment, at the time of production installation, or an idle time before the start of capturing operation. In this case, the radiation imaging apparatus 130 may execute each step in FIG. 4 to approach its state to the state during the operation in the processing shown in FIG. 4. The state of the radiation imaging apparatus 130 can include the elapsed time since a bias voltage is applied to the bias line BsC, the temperature in the radiation imaging apparatus 130, and the elapsed time since the conversion element C is optically reset. The estimation unit 208 can measure the elapsed time by using the timer 214 and measure the temperature by using the temperature sensor 212. The estimation unit 208 may store, in the reference information memory 213, the data obtained by measuring these values a plurality of times and averaging the obtained values. Alternatively, bias current values in various states may be acquired by performing measurement while changing the ambient temperature of the radiation imaging apparatus 130.

During the operation in the processing in FIG. 4, the estimation unit 208 acquires the state of the radiation imaging apparatus 130 when the acquisition unit 205 acquires a bias current value. The estimation unit 208 acquires an estimated value of a dark current by applying this state to a function stored in the reference information memory 213, and outputs the value to the acquisition unit 205. The acquisition unit 205 may acquire an estimated value from the estimation unit 208 every time acquiring a bias current value or may acquire an estimated value once per frame and reuse the value for processing in the same frame.

The present inventors found that in a state in which no radiation is irradiated, the average data of the ith-row image data (to be referred to as dark image data hereinafter) read out from the readout circuit 203 has a correlation with a bias current value when a conductive voltage is applied to a driving line Dri on the ith row. This is because both the dark image data and the bias current value are influenced by variations in the capacity of the conversion element C. Therefore, the estimation unit 208 may acquire dark image data before the start of the operation based on the flowchart of FIG. 4 and store the data in the reference information memory 213. At the time of execution of the operation based on the flowchart of FIG. 4, the estimation unit 208 may estimate the value of a dark current flowing in the bias line BsC when a conductive voltage is applied to the driving line Dri on the ith row by using this dark image data.

In the above embodiment, the determination unit 206 determines in step S404 whether the irradiation of the radiation 123 has started, and determines in step S407 whether the irradiation of the radiation 123 has stopped. However, the radiation imaging apparatus 130 may determine only one of them by using the above method. For example, the radiation imaging apparatus 130 may determine, based on notification from the control computer 140, that the irradiation of the radiation 123 has started, and may determine the end of the irradiation of the radiation 123 by the above method. Alternatively, the radiation imaging apparatus 130 may determine the start of the irradiation of the radiation 123 by the above method, and may determine, based on notification from the control computer 140, that the irradiation of the radiation 123 has stopped, or may perform the above determination based on the lapse of a predetermined period of time.

In the above embodiments, the determination unit 206 uses, as an evaluation value, the value obtained by subtracting an estimated value of a dark current from a bias current value, and determines whether the difference between the evaluation value and the comparison target value falls inside the threshold range. However, the determination unit 206 may determine whether the difference value between the bias current value and the comparison target value falls inside the threshold range corrected by an estimated value of a dark current.

In the above embodiments, the determination unit 206 overwrites an existing evaluation value with an acquired evaluation value in step S405 in FIG. 4. If, however, the evaluation value memory 207 has a sufficient size, the determination unit 206 may store this evaluation value in another memory space without overwriting. In addition, as described above, the determination unit 206 need not store the evaluation value acquired in step S406 in FIG. 4 in the evaluation value memory 207 but may store the evaluation value in the evaluation value memory 207 if it has a sufficient size.

In the above embodiments, the radiation imaging apparatus 130 repeatedly resets the conversion element C during the standby operation of the radiation imaging apparatus 130. If, however, the characteristic fluctuation of the detection unit 201 is stable, it is possible to repeat steps S403 to S405 without performing a reset process. In the above embodiments, the determination unit 206 executes a storage process in step S405 after a determination process in step S404. However, the determination unit 206 may execute a storage process in step S405 between an acquisition process in step S403 and a determination process in step S404. In this case, when storing the evaluation value in the evaluation value memory 207, the determination unit 206 does not overwrite an evaluation value for acquiring a comparison target value to be used for a subsequent determination process.

In the above embodiments, steps S402 to S405 each are performed once in each repetitive operation. However, the embodiments are not limited to this. For example, steps S403 to S405 each may be executed once every time the conversion element C is reset twice. Alternatively, steps S403 to S405 each may be executed twice after the conversion element C is reset once. In addition, the reset period in step S403 may differ from the acquisition period in step S403.

Figure 8:
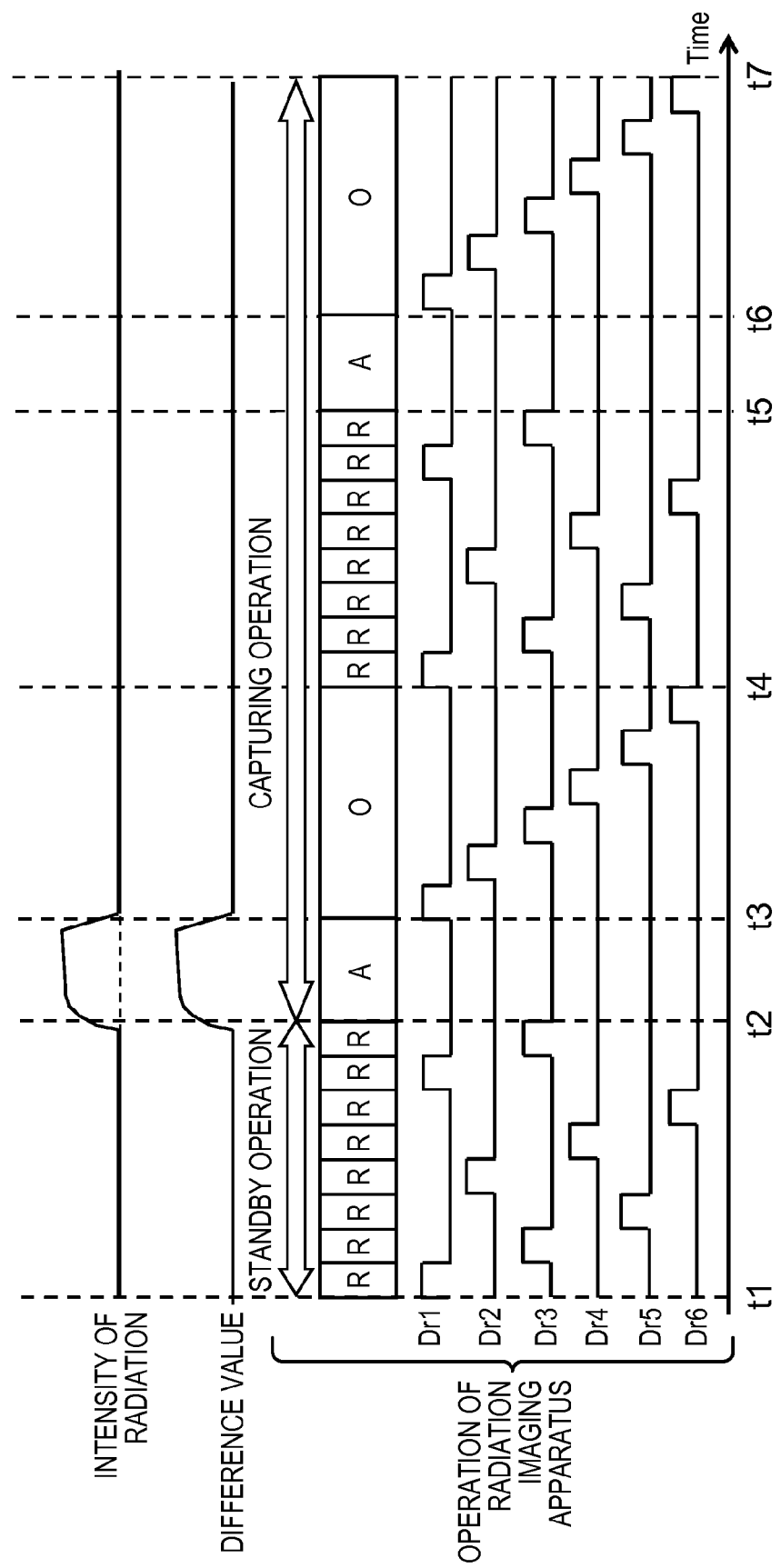
FIG. 8 is a chart for explaining an example of the operation of a radiation imaging apparatus 130 according to an embodiment of the present invention.

In other embodiments of the present invention, in reset operation, the driving circuit 202 applies conductive voltages to only the driving lines Dr on odd-numbered rows first until the last odd-numbered row is set in a conductive state, and then sets the even-numbered rows in a conductive state. FIG. 8 is a chart for explaining an example of a series of operations from the power-on of the radiation imaging apparatus 130 to the output of still image data. The upper graph portion in FIG. 8 represents the intensity of the radiation 123 irradiated onto the radiation imaging apparatus 130. The intermediate graph portion in FIG. 8 represents the difference value between the evaluation value calculated by the determination unit 206 and the comparison target value. The lower graph portion in FIG. 8 represents the operation of the radiation imaging apparatus 130 and indicates the timing of the driving signal supplied to the driving line Dr.

At time t1, the power supply of the radiation imaging apparatus 130 is turned on to start applying a bias voltage to the bias line Bs. With this operation, the radiation imaging apparatus 130 starts standby operation, and the control unit 209 controls the driving circuit 202 to repeat reset operation indicated by "R" in FIG. 8 (between time t1 and time t2 and between time t4 and time t5). In this reset operation, the driving circuit 202 sequentially applies conductive voltages to the plurality of driving lines Dr on only the odd-numbered rows to set the transistors T in a conductive state for each row. When reset operation for the odd-numbered rows is complete, the driving circuit 202 applies a conductive voltage to the first driving line Dr2 on an even-numbered row and sequentially applies conductive voltages to only the even-numbered rows, thereby setting the transistors T in a conductive state for each row. During this reset operation, the control unit 209 controls the acquisition unit 205 and the determination unit 206 to make the acquisition unit 205 acquire the evaluation values based on bias currents and make the determination unit 206 determine whether radiation is irradiated onto the conversion elements C. In the readout operation (indicated by "O" between time t3 and time t4 and between time t6 and time t7 in FIG. 8) of causing the transistors T to transfer accumulated electrical signals to the signal lines Sg, the driving circuit 202 sequentially applies driving voltages to the plurality of driving lines Dr to sequentially set the transistors T in a conductive state for each row.

FIGS. 9A and 9B are views for explaining an example of the values stored in the evaluation value memory 207 to allow the determination unit 206 to acquire a comparison target. Referring to FIG. 9A, let Io[i, j] be the evaluation value acquired by the acquisition unit 205 in step S403 after the application of a conductive voltage to a driving line Drj (j=1, 3, 5) in step S402 on an odd-numbered row in the ith frame (i≥1), and Ie[i, j] be the evaluation value acquired by the acquisition unit 205 in step S403 after the application of a conductive voltage to a driving line Drj (j=2, 4, 6) in step S402 on an even-numbered row in the ith frame (i≥1). For example, Io[K, 1] represents the evaluation value acquired by the acquisition unit 205 after the application of a conductive voltage to the driving line Dr1 in the Kth frame.

When the apparatus performs reset driving for each odd-numbered row and each even-numbered row in the above manner, the determination unit 206 performs a determination process in step S404 by using, as a comparison target value, the evaluation value previously acquired after the application of a conductive voltage to the same driving line Dr. The following is a case in which the determination unit 206 performs determination by using an evaluation value Io[K, 3] acquired after the application of a conductive voltage to the driving line Dr2 in step S402 on an odd-numbered row in the Kth frame. As shown in FIG. 9A, at this point of time, the evaluation value memory 207 stores six evaluation values Io[K−1, 3] to Io[K, 1] stored by the determination unit 206 in the previous three executions of step S405. The determination unit 206 uses, as a comparison target, the evaluation value Io[K−1, 3] used in the last one of one or more previous determination processes in a conductive voltage is applied to the same driving line Dr3 as that in the current determination process and in which the determination unit 206 has determined that the radiation 123 has not been irradiated. The evaluation value Io[K−1, 3] is surrounded by the thick line frame in FIG. 9A. The determination unit 206 determines in step S404 whether the difference value between the evaluation values Io[K, 3] and Io[K−1, 3] as a comparison target, that is, Io[K, 3]−Io[K−1, 3], falls inside the threshold range.

The effect obtained by using, as a comparison target value, the evaluation value I[K−1, 3] previously acquired upon application of a conductive voltage to the same driving line Dr3 will be described with reference to FIG. 10. FIG. 10 is a graph of an evaluation value after the lapse of a sufficient period of time since the power supply of the radiation imaging apparatus 130 is turned on. Fo[n] represents a period during which the radiation imaging apparatus 130 executes operation on only odd-numbered rows in the nth frame. Fe[n] represents a period during which the radiation imaging apparatus 130 executes operation on only even-numbered rows in the nth frame. In each frame, conductive voltages are sequentially applied to the driving lines Dr to reset the conversion elements C. Switching the transistor T between a conductive state and a non-conductive state by applying a conductive voltage to the transistor will cause a current to flow in the bias line Br connected to the same pixel as that to which the driving line Dr is connected. This current is included in the bias current measured by the acquisition unit 205. The present inventors found that a bias current value varies depending on to which driving line Dr a conductive voltage is applied even in the same frame. This seems to be caused by variations in the parasitic capacitance of the transistor T connected to the driving line Dr or the capacitance of the conversion element C. If the variations are large, using the evaluation value used in a previous determination process as a comparison target value is equivalent to comparing evaluation values originating from the application of conductive voltages to the different driving lines Dr. This makes it difficult to accurately detect the irradiation of radiation.

The present inventors, however, found that even if conductive voltages are applied to the driving lines Dr for each odd-numbered row or each even-numbered row, the waveforms of bias currents are similar on a even-numbered or odd-numbered frame basis. For example, as shown in FIG. 10, the waveform of a bias current in an odd-numbered frame Fo[n−1], the waveform of a bias current in a frame Fo[n], and the waveform of a bias current in a frame Fo[n+1] are similar to each other. That is, the evaluation values obtained upon application of conductive voltages to the same driving line Dr become similar to each other even in different frames. It is therefore possible to improve the accuracy of determination by making the determination unit 206 perform a determination process by using, as a comparison target value, the evaluation value I[K−1, 3] previously acquired upon application of a conductive voltage to the same driving line Dr.

Upon determining that the difference value falls inside the threshold range, the determination unit 206 stores the evaluation value Io[K, 3] in the evaluation value memory 207 in step S405. In this case, the determination unit 206 may overwrite the oldest evaluation value I[K−1, 1] among the stored evaluation values. This can save a memory capacity. Upon determining that the difference value does not fall inside the threshold range, the determination unit 206 may not store the evaluation value I[K, 3] in the evaluation value memory 207 for the same reason as that described in the above embodiments. In step S407, the determination unit 206 uses, as a comparison target value, the evaluation value I[K−1, 3] used in the last one of one or more determination processes which have been previously performed for the same driving line Dr and in which the determination unit 206 has determined that the radiation 123 has not been irradiated.

In other embodiments, the determination unit 206 performs a determination process by using, as a comparison target value, the value calculated from the evaluation value previously acquired after the application of a conductive voltage to the driving line Dr adjacent to the same driving line Dr. Consider a case in which the determination unit 206 performs a determination process by using the evaluation value Io[K, 3] acquired after the application of a conductive voltage to the driving line Dr2 in step S402 on an odd-numbered row in the Kth frame. As shown in FIG. 9B, at this point of time, the evaluation value memory 207 stores six evaluation values Io[K−1, 3] to Io[K, 1] stored in the determination unit 206 upon three previous executions of step S405. The determination unit 206 uses, as a comparison target, the evaluation value Ie[K−1, 4] used in the last one of one or more determination processes in which a conductive voltage is applied to the adjacent driving line Dr4 and the determination unit 206 has determined that the radiation 123 has not been irradiated. The evaluation value Ie[K−1, 4] is surrounded by the thick line frame in FIG. 9B. The determination unit 206 determines in step S404 whether the difference value between the evaluation values Io[K, 3] and Ie[K−1, 4] as a comparison target, that is, Io[K, 3]−Ie[K−1, 4], falls inside the threshold range.

According to the description made with reference to FIG. 10, the evaluation values obtained upon application of conductive voltages to the same driving line Dr become similar to each other even in different frames. In addition, since bias currents in an even-numbered frame and an odd-numbered frame have similar waveforms, it is possible to compare a waveform in an odd-numbered frame with an evaluation value by using a waveform in an even-numbered frame. For example, as shown in FIG. 10, bias currents in an even-numbered frame Fe[n−1], a frame Fo[n], and a frame Fe[n+1] have similar waveforms. That is, the evaluation values obtained upon application of conducive voltages to the adjacent driving lines Dr become similar to each other even in different even-numbered and odd-numbered frames. The determination processes in steps S405 and S407 are the same as those in the above embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2012-087936, filed Apr. 6, 2012, and 2013-044726, filed Mar. 6, 2013, which are hereby incorporated by reference herein in their entirety.

What is claimed is:

1. A radiation imaging apparatus comprising:
a plurality of pixels each including a conversion element configured to convert radiation into charge and a switching element configured to transfer an electrical signal based on the charge;
a plurality of driving lines respectively connected to different switching elements of said plurality of switching elements;
a driving circuit configured to apply conductive voltage to said plurality of driving lines to set said switching elements in a conductive state;
bias lines for applying bias voltage to said conversion elements of said plurality of pixels to make said conversion elements convert radiation into charge;
an acquisition unit configured to perform an acquisition process of an evaluation value based on a current flowing in one bias line of said bias lines while said driving circuit is applying the conductive voltage to said plurality of driving lines;
a determination unit configured to perform a determination process of comparing the evaluation value with a comparison target value to determine whether radiation is being irradiated onto said conversion elements;
a control unit configured to control said acquisition unit and said determination unit to perform the acquisition process and the determination process a plurality of times; and
a storage unit configured to store the evaluation value used in the determination process,
wherein a comparison target value used in a given determination process is based on one or more evaluation values used in one or more determination processes which are performed before the given determination process and in which it is determined that radiation has not been irradiated.

2. The apparatus according to claim 1, wherein if it is determined that radiation has not been irradiated in a given determination process, said control unit causes said driving circuit to apply the conductive voltage before execution of a determination process next to the given determination process.

3. The apparatus according to claim 1, wherein a comparison target value used in a given determination process is equal to an evaluation value used in a last one of one or more determination processes which are performed before the given determination process and in which it is determined that radiation has not been irradiated.

4. The apparatus according to claim 1, wherein a comparison target value used in a given determination process is a value calculated from a plurality of evaluation values used in a plurality of last determination processes of one or more determination processes which are performed before the given determination process and in which it is determined that radiation has not been irradiated.

5. The apparatus according to claim 2, wherein said plurality of driving lines are divided into a plurality of groups,
said driving circuit applies the conductive voltage to one of said plurality of groups before execution of the next determination process, and
a comparison target value used in a determination process following application of the conductive voltage to a given group is based on one or more evaluation values used in one or more determination processes which are performed before the determination process after application of the conductive voltage to the group and in which it is determined that radiation has not been irradiated.

6. The apparatus according to claim 5, wherein a comparison target value used in a determination process following application of the conductive voltage to a given group is equal to an evaluation value used in a last one of one or more determination processes which is performed before the determination process after application of the conductive voltage to the group and in which it is determined that radiation has not been irradiated.

7. The apparatus according to claim 5, wherein a comparison target value used in a determination process following application of the conductive voltage to a given group is a value calculated from a plurality of evaluation values used in a plurality of last determination processes of one or more determination processes which are performed before the determination process after application of the conductive voltage to the group and in which it is determined that radiation has not been irradiated.

8. The apparatus according to claim 5, wherein
said plurality of pixels are arranged in a matrix,
each of said plurality of groups includes pixels arranged in a row of the matrix,
each of said plurality of driving lines is connected to said switching elements in a different row of pixels, and
said driving circuit is configured to apply the conductive voltage to even-numbered lines of said plurality of driving lines and then to odd-numbered rows of said plurality of driving lines.

9. The apparatus according to claim 1, wherein said plurality of driving lines are respectively included in different groups, and said driving circuit sequentially applies the conductive voltage to said plurality of driving lines.

10. The apparatus according to claim 9, wherein if it is determined that radiation is irradiated onto said conversion elements, said control unit controls said driving circuit so as not to apply the conductive voltage.

11. The apparatus according to claim 1, further comprising an estimation unit configured to estimate a value of a dark current flowing in said bias line when said acquisition unit acquires the evaluation value,
wherein said acquisition unit calculates the evaluation value by subtracting the value of the dark current from a value of a current flowing in said bias line.

12. The apparatus according to claim 11, wherein said estimation unit estimates the value of the dark current based on an elapsed time since application of bias voltage to said bias line.

13. The apparatus according to claim 11, wherein said estimation unit estimates the value of the dark current based on image data acquired while radiation is not being irradiated onto the radiation imaging apparatus.

14. A radiation imaging system comprising:
a radiation imaging apparatus defined in claim 1; and
a radiation generating apparatus configured to expose said radiation imaging apparatus to radiation.

15. The apparatus according to claim 1, wherein said determination unit is configured to perform the determination process by comparing a difference value between the evaluation value and the comparison target value with a threshold value.

16. A method of controlling a radiation imaging apparatus including a plurality of pixels each including a conversion element configured to convert radiation into charge and a switching element configured to transfer an electrical signal based on the charge, a plurality of driving lines respectively connected to different switching elements of the plurality of switching elements, a driving circuit configured to apply conductive voltage to the plurality of driving lines to set the switching elements in a conductive state, bias lines for applying bias voltage to the conversion elements of the plurality of pixels to make the conversion elements convert radiation into charge, and a storage unit, the method comprising:
an acquisition step of acquiring an evaluation value based on a current flowing in one bias line of the plurality of bias lines while the driving circuit is applying the conductive voltage to the plurality of driving lines;
a determination step of determining whether radiation is being irradiated onto the conversion elements, by comparing the evaluation value with a comparison target value; and
a storage step of storing the evaluation value used in said determination step in the storage unit,
wherein a comparison target value used in a given determination step is based on one or more evaluation values used in one or more determination steps which are performed before the given determination step and in which it is determined that radiation has not been irradiated.

17. The method according to claim 16, wherein the determination step is performed by comparing a difference value between the evaluation value and the comparison target value with a threshold value.

18. A radiation imaging apparatus comprising:
a plurality of pixels each including a conversion element configured to convert radiation into charge and a switching element configured to transfer an electrical signal based on the charge during a conductive state;
a plurality of first lines connected to respective different ones of the switching elements;
a circuit configured to apply conductive voltage to the plurality of first lines to set the switching elements in the conductive state;
second lines for applying bias voltage to the conversion elements of the plurality of pixels to make the conversion elements convert radiation into charge;
an acquisition unit configured to repeatedly acquire values based on a current flowing in the second line while the conductive voltage is applied to the plurality of first lines by the circuit; and
a determination unit configured to compare an amount of change of a first value of the values from one of the conversion elements and a second value of the values from that conversion element with a threshold value to determine whether that conversion element has been irradiated with radiation, the second value being one that has been acquired prior to the first value.

19. The apparatus according to claim 18, further comprising a control unit configured to control the acquisition unit and the determination unit,
wherein if it is determined by the determination unit that the conversion element has been irradiated, the control unit causes the circuit to apply the conductive voltage.

20. The apparatus according to claim 19, wherein the second value is a last-acquired value of one or more values acquired prior to the first value.

21. The apparatus according to claim 19, wherein the second value is an average value of last-acquired values of two or more values acquired prior to the first value.

22. The apparatus according to claim 19, wherein
the plurality of first lines are divided into a plurality of groups,
the circuit applies the conductive voltage at one time to the first lines belonging to one of the plurality of groups, and
the second value after the conductive voltage is applied to a certain group is based on one or more values acquired after the conductive voltage is applied to that group and prior to acquisition of the first value.

23. The apparatus according to claim 22, wherein the second value after the conductive voltage is applied to a certain group is a last-acquired value of one or more values acquired after the conductive voltage is applied to that group and prior to the first value.

24. The apparatus according to claim 22, wherein the second value after the conductive voltage is applied to a certain group is an average value of last-acquired values of two or more values acquired after the conductive voltage is applied to the certain group and prior to the first value.

25. The apparatus according to claim 22, wherein
the pixels are arranged in a matrix,
the plurality of groups are a plurality of rows,
the plurality of first lines are respectively connected to the switching elements in different rows, and
the circuit is configured to apply the conductive voltage to first lines in even rows of the plurality of first lines, followed by applying the conductive voltage to first lines in odd rows of the plurality of first lines.

26. The apparatus according to claim 18, wherein the plurality of first lines are respectively included in different groups, and the circuit applies the conductive voltage to the plurality of first lines sequentially.

27. The apparatus according to claim 19, wherein if it is determined that the conversion element has been irradiated with radiation, the control unit controls the circuit so as not to apply the conductive voltage.

28. The apparatus according to claim 18, further comprising a storage unit configured to store the value and an estimation unit configured to estimate a value of a dark current flowing in the second line when the acquisition unit acquires the value,
wherein the acquisition unit calculates the value by subtracting the value of the dark current from a value of a current flowing in the second line.

29. The apparatus according to claim 28, wherein the estimation unit estimates the value of the dark current based on an elapsed time since application of bias voltage to the second line.

30. The apparatus according to claim 28, wherein the estimation unit estimates the value of the dark current based on image data acquired while the radiation imaging apparatus is not being irradiated with radiation.

31. The apparatus according to claim 18, wherein the acquisition unit acquires the value using an accumulation value of currents flowing in the second line.

32. The apparatus according to claim 18, wherein the amount of change is a difference value between the first value and the second value.

33. A radiation imaging system comprising:
a radiation imaging apparatus according to claim 18; and
a radiation generating apparatus configured to expose the radiation imaging apparatus to radiation.

34. A method of controlling a radiation imaging apparatus including a plurality of pixels each including a conversion element configured to convert radiation into charge and a switching element configured to transfer an electrical signal based on the charge during a conductive state, a plurality of first lines connected to respective different ones of the switching elements, a circuit configured to apply conductive voltage to the plurality of first lines to set the switching elements in the conductive state, and second lines for applying bias voltage to the conversion elements of the plurality of pixels to make the conversion elements convert radiation into charge, the method comprising:
acquiring values based on a current flowing in the second line while the conductive voltage is applied to the plurality of first lines by the circuit; and
comparing an amount of change of a first value of the values and a second value of the values with a threshold value to determine whether radiation has been irradiated onto the conversion element, the second value being acquired prior to the first value.

* * * * *